United States Patent
Fine et al.

(10) Patent No.: US 7,758,505 B2
(45) Date of Patent: Jul. 20, 2010

(54) METHODS AND APPARATUS FOR NON-INVASIVE DETERMINATION OF PATIENT'S BLOOD CONDITIONS

(75) Inventors: Ilya Fine, Rehovot (IL); Leonid Shvartsman, Rehovot (IL)

(73) Assignee: ELFI-Tech Ltd., Rehovot (IL)

( * ) Notice: Subject to any disclaimer, the term of this patent is extended or adjusted under 35 U.S.C. 154(b) by 351 days.

(21) Appl. No.: 11/604,401

(22) Filed: Nov. 27, 2006

(65) Prior Publication Data

US 2007/0232940 A1 Oct. 4, 2007

Related U.S. Application Data

(60) Provisional application No. 60/788,074, filed on Apr. 3, 2006.

(51) Int. Cl.
*A61B 5/00* (2006.01)
(52) U.S. Cl. .................. 600/368; 600/504; 600/367
(58) Field of Classification Search ............... None
See application file for complete search history.

(56) References Cited

U.S. PATENT DOCUMENTS

| | | | |
|---|---|---|---|
| 5,282,467 A * | 2/1994 | Piantadosi et al. | 600/335 |
| 5,869,044 A | 2/1999 | Tomaru et al. | |
| 6,146,327 A | 11/2000 | Wilk | |
| 6,322,525 B1 | 11/2001 | Kensey et al. | |
| 6,551,266 B1 | 4/2003 | Davis, Jr. | |
| 6,587,704 B1 | 7/2003 | Fine et al. | |
| 7,544,168 B2 * | 6/2009 | Nitzan | 600/495 |
| 2002/0032149 A1 | 3/2002 | Kensey | |
| 2004/0138563 A1 | 7/2004 | Moehring et al. | |
| 2004/0180051 A1 | 9/2004 | Suzuki | |
| 2005/0101846 A1 | 5/2005 | Fine et al. | |
| 2006/0247538 A1 | 11/2006 | Davis | |

FOREIGN PATENT DOCUMENTS

WO  03051208 A1  6/2003

OTHER PUBLICATIONS

EP 07736131 Supplementary Partial European Search Report, mail date of Feb. 5, 2010.

* cited by examiner

*Primary Examiner*—Robert L Nasser
(74) *Attorney, Agent, or Firm*—Browdy and Neimark, PLLC

(57) ABSTRACT

A method and apparatus are presented for non-invasive determination of blood clotting related and blood circulation related parameters of a mammal. At least one stimulus ST is non-invasively induced in a blood containing medium in the mammal for a preset period of time $t_{ST}$. This at least one stimulus is selected to cause at least one of the following to occur: (a) inducing at least two of three Virchow's triad elements including abnormalities of blood flow; abnormalities of blood constituents and abnormalities of the blood vessel wall, and (b) inducing a change in red blood cell (RBC) aggregation or local blood viscosity. Measurements are non-invasively performed at a measurement location in the mammal by applying an external field thereto for a preset time period $t_m$, a response of the measurement location to the applied field is detected, and measured data indicative thereof generated. At least a portion of the measured data and stimulus related data are processed so as to determine a relation between a time function of the at least one stimulus ST(t) and a time function of the measured data OR(t). This relation is indicative of at least one blood circulation and blood coagulation related parameter of the mammal.

31 Claims, 4 Drawing Sheets

METHODS AND APPARATUS FOR NON-INVASIVE DETERMINATION OF PATIENT'S BLOOD CONDITIONS

FIELD OF THE INVENTION

This invention is generally in the field of non-invasive determination of patient's blood conditions, and relates to a method and apparatus for determining blood clotting and circulation related parameters.

BACKGROUND OF THE INVENTION

The proper control of blood clotting is essential to the health of a mammal. Both the insufficient clotting that leads to bleeding is a serious problem for some individuals, and the increased tendency to clot resulting in stroke, myocardial infarction, or deep vein thrombosis, are also dangerous to the individual.

Blood coagulation is a complex defensive mechanism. Blood clotting is essential to prevent hemorrhage from damaged blood vessels. A thrombus is a clot in the blood vessels. Blood does not normally clot in the vascular system, since thrombin is present in the inactive form, prothrombin, which becomes activated to thrombin when blood escapes due to injury or is withdrawn from the blood vessels.

Thrombi can form in response to changes in the blood vessel wall to which platelets adhere. The final stage of clotting process is turning of fibrinogen, which is soluble and optically invisible, into fibrin which is insoluble. The fibrin separates as long fibers or threads, which are extremely adhesive. These threads stick to each other, blood cells, tissues, and foreign substances to form a three dimensional network or clot. The formation of a clot is the final event in the blood coagulation cascade. Fibrinogen plays a key role in the final stage of clotting There is another important phenomenon associated with blood fibrinogen: In the presence of fibrinogen and globulin, red blood cells tend to form aggregates known as rouleaux. An abundance of fibrinogen has a greatest impact on the elevation of aggregation rate in blood.

Some methods for treating and/or measuring blood flow are exemplified by the following publications:

U.S. Pat. No. 5,869,044 to Tomaru et al., discloses a method for the treatment or prophylaxis of ischemia-reperfusion injury including administration of batroxobin as an effective component;

U.S. Pat. No. 6,322,525 to Kensey et al., discloses a method of analyzing data form a circulating blood visocometer for determining absolute and effective blood viscosity;

U.S. Pat. No. 6,551,266 to Davis, Jr., describes rheological treatment methods and related apheresis systems for removing certain rheologically active elements from the blood of a patient;

US 2004/0180051 to Suzuki, discloses blood rheology improving agents including an antibody against human tissue factor (human TF);

US 2004/0090614 to Greco discloses spectral analysis of light scattered from clotting blood. The method comprises irradiating a specimen with light and recording light reflected into the hemisphere of the irradiating beam. The time course of the reflected light intensity is divided into distinct regions, each of which is fitted to a mathematical formula. The parameters from these formulae are used to assign values to each specimen. The assigned values identify disease states and quantify the effects of drugs on clotting.

SUMMARY OF THE INVENTION

This invention is directed to a non-invasive method and apparatus for determining blood clotting and circulation related parameters of a mammal, to thereby estimate a risk condition in the mammal health, e.g. a risk of blood abnormalities and thrombi.

The present invention takes advantage of the Virchow postulates consisting in that three features predispose to thrombus formation: (i) abnormalities of blood flow; (ii) abnormalities of blood constituents and (iii) abnormalities of the blood vessel wall. The inventors have found that by non-invasively inducing at least one stimulus in a blood containing medium in the mammal, so as to cause at least two of said three Virchow's triad elements to occur, and/or to cause a change in red blood cell (RBC) aggregation or local blood viscosity, the blood-containing medium condition allows for non-invasively measuring the blood circulation and blood coagulation related parameters of the medium. The measurements are taken by subjecting the medium under said conditions to an external field, and detecting a response of the medium to the applied field. The applied field may be an appropriate electromagnetic field (i.e. time variant electromagnetic field as light and/or microwave and/or RF field), in which case the response may be in the form of electromagnetic and/or acoustic radiation (i.e. pure-optic or photo-acoustic measurements); or the applied field may be a DC or RF electric field, the measured response being an electrical signal indicative of a change in the impedance of the medium.

According to one broad aspect of the invention, there is provided a non-invasive method for determination of blood clotting related and blood circulation related conditions of a mammal, the method comprising:

(i) non-invasively inducing at least one stimulus ST in a blood containing medium in the mammal for a preset period of time $t_{ST}$, said at least one stimulus being selected to cause at least one of the following to occur: (a) inducing at least two of three Virchow's triad elements including abnormalities of blood flow; abnormalities of blood constituents and abnormalities of the blood vessel wall, and (b) inducing a change in red blood cell (RBC) aggregation or local blood viscosity;

(ii) performing non-invasive measurements at a measurement location in the mammal by applying an external field thereto for a preset time period $t_m$; detecting a response of the measurement location to the applied field; and generating measured data indicative thereof; and (iii) processing at least a portion of the measured data and processing stimulus related data so as to determine a relation between a time function of said at least one stimulus ST(t) and a time function of the measured data OR(t), said relation being indicative of at least one blood circulation and blood coagulation related parameter of the mammal.

The results of such non-invasive technique provides for predicting a risk in the patient's health (e.g. a condition of thrombosis), as well as controlling the effectiveness of the previous drug-based treatment. Generally, the condition to be determined relates at least one of the following: a condition of thrombosis, risk of bleeding, and prothrombin time. The condition(s) to be determined are defined by at least one of the following parameters of the medium: a blood viscosity, a blood rheological property, a blood density; RBC aggregation rate, prothrombin time; a blood optical property; a blood coagulation parameter; a plasma protein parameter; an erythrocyte sedimentation rate; a fibrin concentration; a fibrinogen concentration; and a drug concentration or concentration of certain product of drug metabolism.

The at least two selected Virchow's triad elements preferably include an abnormality of blood flow, and an abnormality of a blood constituent, and may also include an abnormality of the blood vessel wall. Thus, the induced stimulus or stimuli may be such as to cause a change in the blood flow and/or a change in the blood chemistry and/or the blood vessel integrity, and/or to cause a change in the local blood viscosity (by changing a local RBC aggregation state or local blood hematocrit or both).

The abnormality of blood flow may be one or more of the following: an abnormality of the blood rheology; an abnormality of turbulence at bifurcations; an abnormality of turbulence at a stenotic region; an abnormality of blood viscosity or localized viscosity of the blood. The abnormality of a blood constituent may be one or more of the following: an abnormality of hemocrit and haemoglobin concentration, an abnormality of a coagulation pathway; an abnormality of a fibrinolytic pathway; an abnormality of plasma fibrinogen concentration, an abnormality of plasiminogen activator inhibitor concentration, an abnormality of tissue plasminogen activator concentration, an abnormality of fibrin degradation product concentration selected from a fibrin D-dimer, homocysteine concentration, a von Willebrand factor concentration; an anemic abnormality, and a drug concentration or concentration of drug metabolism related components. The abnormality of the blood vessel wall may be an abnormality of the endothelium, and/or a blood vessel wall thickness, and/or a blood vessel wall rigidity, and/or a blood vessel wall roughness and a plaque concentration.

Thus, the induced stimulus or stimuli may be such as to cause a change in the blood flow and/or a change in the blood chemistry and/or the blood vessel integrity, and/or to cause a change in the local blood viscosity (by changing a local RBC aggregation state and/or local blood hematocrit).

Preferably, the two selected Virchow's triad elements are abnormality of blood vessel wall and abnormality of blood flow (stasis).

The at least one stimulus may be induced in the vicinity of the measurement location or at a location on the mammal remote from the measurement location. For example, one stimulus is induced in the vicinity of the measurement location; and the other is induced at a remote location.

The optical, acoustic or electric signal is related to at least one blood parameter selected from: a blood viscosity, blood rheological properties, a blood density; a blood optical property; a blood coagulation parameter; a plasma protein parameter; an erythrocyte sedimentation rate; a fibrin concentration; a fibrinogen concentration; and a drug concentration.

According to some embodiments of the invention, the non-invasive measurement includes subjecting the measurement location to an external electromagnetic field (light field), detecting an optical and/or acoustic response from the measurement location to the applied field, and generating measured data indicative thereof. This can be pure-optical measurements and/or photo-acoustic measurements. According to some other embodiments of the invention, the non-invasive measurement includes measurement of an impedance of a media at the measurement location.

Preferably, the invention utilizes pure optical measurement and is therefore described below with respect to this specific but not limiting example.

Preferably, a time dependence of the induced stimulus is controlled during a preset period of time $t_{ST}$, while keeping this time dependence in a preset manner (e.g. a function $\sin(\omega t)$) for time t, where $t < t_{ST}$.

According to some embodiments of the invention, the response (e.g. optical response) of the measurement location is fixed after a certain delay time $t_d$ from the application of the at least one stimulus. It should be noted that this time delay $t_d$ may be positive, zero or negative. For example, the fact that the time delay $t_d$ is negative means that the measurement session (during which the optical response is detected) starts before the end of the stimulus/stimuli application; when the time delay $t_d$ is zero the measurement starts precisely at the instant when the stimulus/stimuli end(s); and when the time delay $t_d$ is positive the measurement session starts after the application of the stimulus/stimuli is complete.

For example, a stimulus, e.g. in the form of a light pulse of a specific wavelength (e.g. green), is applied for a certain time period (e.g. $t_{ST}=1$ sec), and a measurement, e.g. optical measurement, starts a certain time thereafter (e.g. $t_d=0.5$ sec). The measurement consists for example of measuring a time evolution of IR transmission of the measurement location during a certain measurement time (e.g. 20 sec). The entire measurement of a time dependence of the response continues during a time period $t > t_d$ (time from the end of stimulus application until the start of measurement).

Considering the negative time delay $t_d$, the optical measurement session may be halted before or after the end of stimulus/stimuli application. For example, the application of stimulus (e.g. green light) varies as $\sin(\omega t)$ for $t=0$ sec (as indicated above the preset time period $t_{ST}$ during which the application of stimulus is controlled may be greater than this time t of the predetermined function of the stimulus variation); 0.5 sec after the application of stimulus starts, the time evolution of IR transmission is measured during a first stage concurrently with the application of stimulus (i.e. for a time period $t_1 < 10$ sec), and afterwards during a second stage, e.g. for a time period $t_2 < 20$ sec. The data analysis may for example include determination and analysis of a phase shift in the first measurement stage and decrement of the decay at the second measurement stage.

Generally, the analysis of measured data is aimed to determine a relation between the time variation of the at least one stimulus $ST(t)$ and the time variation of the response (e.g. optical) $OR(t)$. The measurement of the time dependence of the optical response is preferably carried out for at least two different wavelengths of the applied light field. Hence, the measured data is indicative of the optical response as a function of time and wavelength, and the relation between the induced stimulus and the optical response is a function of wavelength of the applied field and the time parameter $t_{ST}$ and possibly also time parameter $t_d$, if needed.

Considering the pure-optical measurements, said at least two different wavelengths of the applied light field are in a visible-NIR range.

The relation between the optical response and the applied stimulus/stimuli is a predetermined mathematical manipulation (functional), for example a convolution, between the time function of the stimulus/stimuli $ST(t)$ and the time and wavelength function of the optical response $OR(t,\lambda)$.

For example, a pressure (first stimulus) is applied as a function $ST_1(t)=$Const for a time $t_1 < t_{ST1}$, and a short strong green light pulse (second stimulus) $ST_2(t)=$Const is applied between the time instants $t_{2i}=t_{ST2} < t_{ST1}$ and $t_{2f}=t_{ST2}+\delta t_{ST2} > t_{ST1}$ where $t_{ST1}$ and $\delta t_{ST2}$ are the durations of the first and second stimuli while varying with time in certain predetermined manner. Then, an optical measurement is carried out during a time $0 < t < 3(t_{ST2} + \delta t_{ST2})$, i.e. a change of the shape (profile) of the optical response (IR transmission) varies during this time $0 < t < 3(t_{ST2} + \delta t_{ST2})$. The profile of the optical response at time $t < t_{ST1}$ is analyzed, its parameters are processed, and then the change in the optical response after time $t_{ST2}$ till the end of the measurement procedure is determined.

The processing result is indicative of the blood clotting and/or blood flow circulation related parameter. It should be understood that to this end, certain reference data is used (e.g. being the results of previously conducted calibration stage) representative of the blood related parameter(s) value(s) and values corresponding to said relations.

Generally, the stimulus may include: application of mechanical pressure P and/or local heat H and/or short strongly absorbable laser pulse I of a preset time dependence (e.g. application of stimulus and then release thereof) to the mammal at a location remote from the measurement location (e.g. at a location upstream of the measurement location with respect to a normal blood flow direction) and/or at the vicinity of the measurement location. The stimulus may include at least two of the following: mechanical pressure application (e.g. short over-systolic pressure), heat application and laser pulse application, being functions of preset time P(t), H(t) and I(t) respectively (generally ST(t)). The relation between the stimuli functions and the optical response OR(t) is determined as a mathematical manipulation (function, e.g. convolution) of OR(t) and P(t), H(t) and I(t), meaning certain functional of $\{OR(t), ST(t)\}$, $\{OR(t), H(t), I(t), \text{and } P(t)\}$. Each of the functions P(t), H(t) and I(t) may be characterized by its own time scale $t_{STi}$ different from the other(s), the measured optical response depending on all the time scales. The blood condition in the mammal may be extracted from the dependence of the relation between ST(t) and OR(t) on the wavelength of incident light and said time scales.

The stimulus/stimuli may include inducing a micro-injury in either one of endothelial cells, venulas and arterioles, the measured time dependence of the light response being indicative of various stages of consequences of the injury. The stimulus/stimuli may occur over said time scales $t_{STi}$ and may include laser micro-injury, blood stasis, released blood flow and blood flow modulated in a certain pre-determined way. At least one of said times scales of the stimuli and/or the time delay $t_d$ may for example vary from 0 till 540 seconds.

The method may further include application of at least one treatment to the mammal, where said treatment is of a kind responsive to the risk. The treatment is selected from a mechanical treatment; an electromagnetic treatment; a drug treatment; etc.

According to another broad aspect of the invention, there is provided a non-invasive method for use in determining blood clotting and circulation related parameters of a human, the method comprising:

(i) inducing, during a first time period $t_{ST}$, at least one stimulus that non-invasively causes one of the following to happen: inducing at least two of three Virchow's triad elements and the change in RBC aggregation in a blood containing medium of the human, wherein the blood comprises a concentration of at least one drug selected from blood thinners and products of the metabolism of this drug;

(ii) non-invasively measuring at least one optical, acoustic and electric signals at a measurement location in the blood containing medium of the human for a preset time period t; and generating measured data indicative thereof;

(iii) processing the measured data and the stimulus related data so as to determine a relation between the time function of said at least one stimulus and the time function of the measured data, said relation being indicative of at least one of the blood clotting related and blood circulation related parameters;

(iv) controlling, by measuring said at least one blood parameter, at least one treatment administered to said human, where said at least one treatment is of the kind affecting said blood clotting related and blood circulation related parameters.

According to yet another broad aspect of the invention, there is provided a non-invasive method for use in optically controlling the determination at least one physico-chemical rheology connected property of a patient's blood, the method comprising:

inducing at least one stimulus ST as a function of time ST(t) in the patient so as to at least slightly modulate the state of the patient, during a time period $t_{ST}$;

applying optical measurements to a measurement location in the patient after a certain delay time $t_d$ from the induced stimulus, the optical measurement comprising detection of an optical response from the measurement location to at least two different wavelengths of incident light;

measuring a time dependence of the optical response, OR(t) for a time period t greater than said certain time delay $t_d$;

determining a relation between the time function ST(t) and the optical response being a function of time and wavelength OR(t,λ), said relation being indicative of at least one rheological blood parameter.

According to yet another aspect of the invention, there is provided an apparatus for use in non-invasive determination of blood clotting related and blood circulation related parameters in a mammal, the apparatus comprising:

(a) a measurement unit configured and operable for applying an external field to a measurement location in a blood containing medium of the mammal, detecting a response from the measurement location to the applied field, and generating measured data indicative thereof;

(b) a stimulus inducing device configured and operable to induce at least one stimulus in the blood containing medium in the mammal, said at least one stimulus being of a kind causing at least one of the following to occur: (i) inducing at least two of three Virchow's triad elements in the medium including abnormalities of blood flow; abnormalities of blood constituents and abnormalities of the blood vessel wall; and (ii) inducing a change in the RBC aggregation;

(c) a control unit configured for selectively operating said stimulus inducing device to maintain each of said at least one stimulus for a preset period of time $t_{ST}$, for operating the measurement unit to perform measurements and generate the measured, said control unit being preprogrammed to process and analyze the measured data to determine a time function of at least a portion of the measured data and a time function of said at least one stimulus and determine a relation between the time variations of said at least one stimulus and the at least portion of the measured data, said relation being indicative of the blood clotting related and blood circulation related parameters in the mammal.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

This invention is directed to in vivo methods and apparatus for determining risk of blood abnormalities, such as thrombi, in a mammal.

Figure 1:
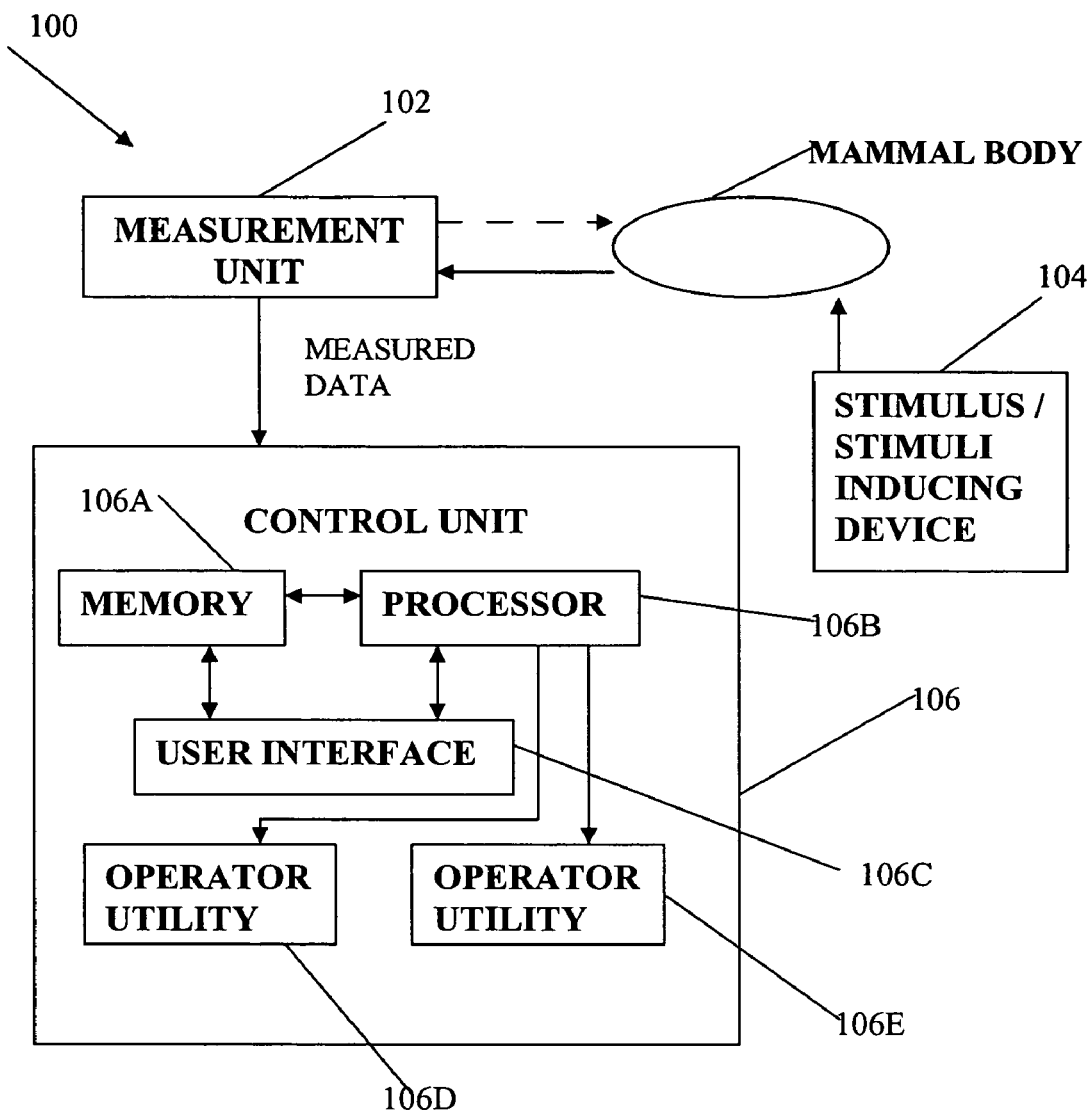
FIG. 1 is a schematic illustration of a system of the present invention for non-invasive measurement of a blood condition in a mammal.

FIG. 1 schematically illustrates an apparatus 100 configured and operable according to the invention for use in non-invasive determination of blood-related parameters indicative of physico-chemical rheology connected property of blood, such as risk of thrombosis in a mammal. Apparatus 100 includes a measurement unit 102, a stimulus inducing device 104, and a control unit 106.

Measurement unit 102 is configured to be applied to a measurement location on a blood medium of the mammal to cause the generation of and detect optical and/or acoustic and/or electric response(s) from the measurement location. Generally, the measurement unit may be configured for carrying out at least one of the following types of measurements:

The measurement unit may carry out pure optical measurements, namely may include a source of an external electromagnetic field (light source) for illuminating the measurement location with light (one or more wavelengths) of a predetermined spectra (e.g. red-NIR spectra), and a light detector unit for detecting the light response of the measurement location, i.e. light transmitted through and/or reflected (scattered) from the measurement location. If the stimulus to be induced is optical (e.g. laser pulse), then the measurement unit and the stimulus inducing device may utilize the same light source which is selectively operated for inducing the stimulus and the optical response for measurements.

The measurement unit may be configured for carrying out photo-acoustic measurements, namely may include a source of an external electromagnetic field (light source) configured and operable for generating light in a wavelength range where the scattering or absorbing properties of the mammalian blood are sensitive to provide an acoustic response, and an acoustic detector unit for detecting the acoustic response of the measurement location.

The measurement unit may be configured for measuring impedance of at least a portion of the medium at the measurement location, namely may include electrical current generator and current/voltage response detection unit. If the stimulus to be induced is an electrical field, then the same electrical current generator can be used for both the stimulus inducing and the electrical impedance measurement.

As indicated above, in a preferred embodiment of the invention the measurement unit is configured for carrying out pure optical measurements, and the invention will therefore be described below for this specific example, but it should be understood that the invention is not limited to this example. Thus, according to one possible not limiting example, the measurement unit is configured and operable to apply an external electromagnetic field to the measurement location, detect an electromagnetic radiation response of the medium to the applied field, and generate measured data indicative of the detected response.

It should be noted that the light source contained in the measurement unit which is brought to a measurement location may be a light emitting unit itself which may or may not be associated with an optical window made in the housing of the measurement unit (e.g. using light guiding arrangement such as fiber), or may be constituted by such an optical window coupled to a light emitter located outside the measurement unit.

Stimulus inducing device 104 includes one or more stimulus inducing units. The latter is/are configured and operable to create at least one of the following in the measurement location: at least two of three Virchow's triad effects, and a change in the RBC aggregation or local blood viscosity. As indicated above, the Virchow's triad elements include (i) abnormalities of blood flow; (ii) abnormalities of blood constituents; and (iii) abnormalities of the blood vessel wall. The stimulus may be of the kind to be applied to the measurement location or to a location of the medium remote from the measurement location, for example to be applied to a location on the mammal upstream of the measurement location with respect to a normal blood flow direction in the mammal.

The stimulus inducing unit is operable by the control unit to temporarily apply the respective stimulus, so as to for example create the so-called "mini-thrombosis" condition in the mammal. Thus, the stimulus is induced for a preset period of time $t_{ST}$, being thus generally a function of time $ST(t)$. The stimulus is kept in a preset manner for a time period t (not exceeding time $t_{ST}$).

The stimulus may be constituted by a mechanical pressure P applied to a location on the mammal (e.g. on patient's hand or finger), thus $ST(t)=P(t)$. This may include pressure application to a location upstream of the measurement location with respect to a normal blood flow direction, and/or pressure application at the measurement location (in the vicinity thereof). Alternatively or additionally, the stimulus may include heat H applied to the mammal, thus $ST(t)=H(t)$, where the heat may be applied to the measurement location and/or a location on the mammal remote from the measurement location (e.g. upstream of the measurement location). Alternatively or additionally, the stimulus may include application of a short strongly absorbing laser pulse I, thus $ST(t)=I(t)$, at the measurement location and/or upstream thereof.

It should be understood that as heat and short pulse applications may be implemented by applying a light field, the same light source of the measurement unit may be used for both creating the stimulus (e.g. heat) and applying the light field for measurements.

It should also be noted that the stimulus (e.g. laser/heat application or ultrasonic radiation for example) may induce an injury (e.g. micro-injury) in endothelial cells and/or venulae and/or arterioles of the mammal. Measured time dependence of the light response may thus be indicative of various stages of consequences of such an injury.

Control unit 106 is typically a computer system including inter alia a memory utility 106A, a data processing and analyzing utility 106B, and user interface 106C. For the purposes of the present invention, the control unit includes a measurement operator utility 106D and a stimulus operator utility 106E.

Stimulus operator utility 106E is selectively operable by processor 106B for selectively actuating the at least one stimulus inducing device for inducing one or more stimuli and maintaining it/them for predetermined period(s) of time. Measurement operator utility 106D is operable by processor 106B for selectively operating the measurement unit to provide first measured data $MD_1$ corresponding to a normal condition of the medium under measurements (with no stimulus) and second measured data $MD_2$ corresponding to the medium condition resulting from the induced one or more stimuli, e.g. the induced at least two Virchow's triad elements and/or induced change in red blood cell (RBC) aggregation or local blood viscosity.

Processor 106B is preprogrammed with certain mathematical model(s) for processing the measured data coming from the measurement unit and determining time dependence thereof, and for analyzing the first and second time dependencies (i.e. time functions of the stimulus and the measured response) to identify the presence of a predetermined condition of the blood, e.g. a condition indicative of the risk of thrombosis in the mammal. The mathematical model provides for determining a relation (a predetermined mathematical manipulation or function) between the time dependences of the detected signal (response) from the medium (e.g. optical signal) and the time dependence of the one or more stimuli.

As indicated above, optical measurements are preferably applied with more than one wavelengths of incident light. Hence, the processor determines the measured optical response as a function of both time and wavelength. The use of more than one wavelength is preferred as it appears that an optical response to some wavelengths increase reaching asymptotic behavior, while some other show no such behavior.

Figure 2:
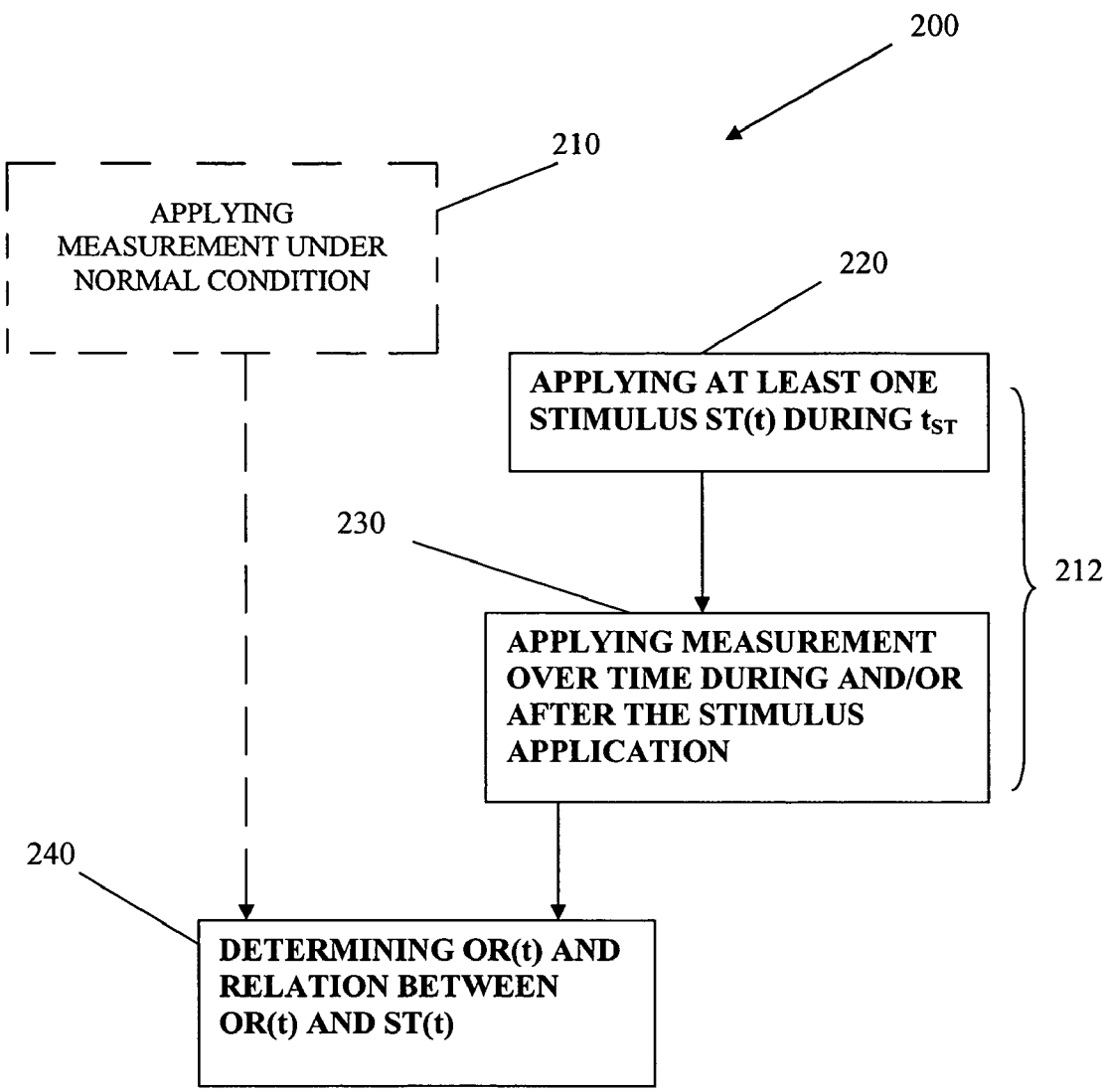
FIG. 2 is an example of a method of the present invention for non-invasively determining a risk condition of blood.

Reference is made to FIG. 2 exemplifying a flow chart 200 of an example of a method of the present invention. This example is based on the pure optical measurements, but as indicated above the invention should not be construed as being limited to this specific implementation.

Optionally, a measurement of an optical response during a preset time period $t_0$ is taken (step 210) at a normal condition of the medium, and first measured data $MD_1$ is provided and stored in the memory utility. The first measured data might present some kind of reference data, which for a specific patient may be taken once for multiple sessions of actual measurements (i.e. measurements under the stimulus).

Preferably, a database of reference data is previously created at a calibration stage and stored in the memory utility. Additionally or alternatively, a library of reference data can be created for each set of two Virchow's elements and stored in the memory utility for use in calibration for one or more patients/mammals.

Actual measurements are applied to the measurement location (step 212). To this end, one or more stimuli, ST, is/are controllably applied to the medium for a time period $t_{ST}$ to induce e.g. at least two of the Virchow's elements (step 220). As indicated above, this stimulus is controlled to be a certain predetermined function ST(t) during a time interval t of said time period $t_{ST}$. Optical measurements are applied to the medium over time during and/or after the stimulus application, preferably using more than one wavelengths of incident light, and the light response is detected during a preset time period (step 230). As indicated above, the optical measurement session may and may not overlap with the stimulus/ stimuli application period, namely, the measurement of the optical response can start a certain time $t_d$ after the stimulus application is completed (positive time delay $t_d$), or starts precisely at the instant when the stimulus ends (zero time delay $t_d$), or may start before the application of the stimulus is completed (negative time delay $t_d$).

In an analysis step 240, a relation (mathematical manipulation or function) between the measured data function (function of time and wavelength) and the applied stimulus time function is determined so as to provide output data indicative for example of a thrombosis condition and thrombus formation time. The output data may for example be in the form of a convolution of ST(t) and OR(t, $\lambda$).

The output data may be stored in the memory utility, and may be used to determine at least one of the following: a risk level associated with at least one disease or condition; a degree of a least one disease or condition; and an anomaly in at least one of the three Virchow's effects.

As indicated above, this invention is based on understanding of that when two out of three Virchow's triad elements ((i) abnormalities of blood flow: (ii) abnormalities of blood constituents and (iii) abnormalities of the blood vessel wall) coincide, then blood clotting event likelihood is increased significantly. Two of these components may be selected from any combination of two components from any two corresponding groups of the three groups listed hereinbelow.

(i) Abnormalities of blood flow relate to, but are not limited to, abnormalities of the blood rheology and turbulence at bifurcations and stenotic regions. Blood flow also relates to the viscosity or local viscosity of the blood.

(ii) Abnormalities of blood constituents include, but are not limited to, abnormalities in coagulation and fibrinolytic pathways. Abnormalities of blood constituents include, but are not limited to, plasma fibrinogen concentration, plasiminogen activator inhibitor concentration, tissue plasminogen activator concentration, fibrin degradation product concentration.

(iii) Abnormalities of the blood vessel wall include, but are not limited to, abnormalities of the endothelium, thickness, rigidity and roughness of the wall and plaque concentration.

Typically, a thrombosis is more likely to occur in an extremity (leg or arm, generally body peripheral organs) than within the chest or abdomen. Blood clots occur most often in the legs and often after prolonged periods of immobility.

In some embodiments, one of the two selected Virchow's triad elements is an abnormality of blood flow. The other of the two selected Virchow's triad elements may be an abnormality of a blood constituent.

In some embodiments of the invention, the method of the present invention can be used to predict the effect of at least one drug present in the blood on a risk (degree of risk) of thrombosis, internal bleeding or other risk effects. In step 210, the measurements may relate to light response outputs of blood containing the at least one drug and in step 230, the light response outputs of the blood containing the at least one drug, following stimulation in step 220. The output (processed) data of step 240 may be used preventatively and/or to take further steps to treat the patient/mammal.

In some preferred embodiments of the present invention, it is aimed to predict the risk of thrombosis or other anomalous condition in a human. Accordingly, the measurement technique and data processing model are aimed to determine clotting time, which is the time that blood takes to stop flowing. The thrombin clotting time is a measure of thrombin/ fibrinogen status. The blood clotting time determination in vitro is based on mechanical or optical tracking of the changes occurring when fibrinogen is converted into fibrin.

To date most of the methods for determine blood clotting are performed in vitro, such as by employing frequent use of a photo-optical device to measure changes in light scattering of a blood sample, and wherein the degree of change is proportional to the fibrinogen concentration. A Prothrombin Time (PT) Test is one of the most common ways of expressing the clotting tendency of blood. PT test results are reported as the number of seconds the blood takes to clot when mixed with a thromboplastin reagent.

Blood thinning drugs and anticoagulants act to prevent blood clots and blockages of arteries. Some of these drugs, like aspirin, reduce the stickiness of blood platelets. Others, such as anticoagulant drugs, impede blood clotting factors. Common anticoagulants include coumadin (warfarin) and heparin. The use of all of these types of drugs must be performed under close medical supervision as overdosing of any of these agents may induce severe bleeding and death. These drugs have a "narrow" therapeutic range such that, on the one hand, an overdose of a blood thinner can cause hemorrhage, whereas, on the other hand, an underdose can allow clots to form and obstruct blood vessels, causing stroke or death.

PT/INR tests are needed at periodic intervals throughout the course of therapy to guide dosage recommendations. The goal of this precise monitoring is to maintain the safest and most effective blood levels of the anticoagulant for your specific medical condition.

In order to meet the clinical demand of management of anticoagulant drug dosage, similar to a diabetic glucose monitoring system, the home based devices, which require only a small drop of blood using the finger stick method was recently developed and cleared for use. One of disadvantages of such in-vitro measurement of coagulation process is that it does not necessarily reflect the coagulation process in the body whereas the blood vessels are actively involved into the process. Introducing non-invasive device will enable not only painless and frequent measurement of blood coagulation status but will provide the patient or the physician with more adequate information how appropriately to fit the drug for the patient.

In some further embodiments, the above-described method of flowchart 200 may be used as a basis for further treatments responsive to a risk level associated with at least one disease or condition; a degree of a least one disease or condition; and an anomaly in at least one of the three Virchow's effects.

Once the risk has been determined for an individual, at least one treatment could be applied to said mammal responsive to the risk. The treatment may be a mechanical treatment and/or an electromagnetic treatment and/or a drug treatment and/or a polymer treatment and/or a psychological treatment. The mechanical treatment may be a mechanical movement treatment, a hypobaric treatment, a hyperbaric treatment, a blood filtration treatment, and/or an ultrasonic treatment. The electromagnetic treatment may be a laser treatment, an infra-red treatment and/or an ultraviolet treatment. The drug treatment may be a statin treatment, an antibody treatment, and/or an anticoagulant treatment. The polymer treatment may be a drag reducing polymer treatment and/or blood polymer treatment. The psychological treatment may be a hypnotic treatment, a conditioning treatment, and/or behaviorism treatment.

Figure 3:
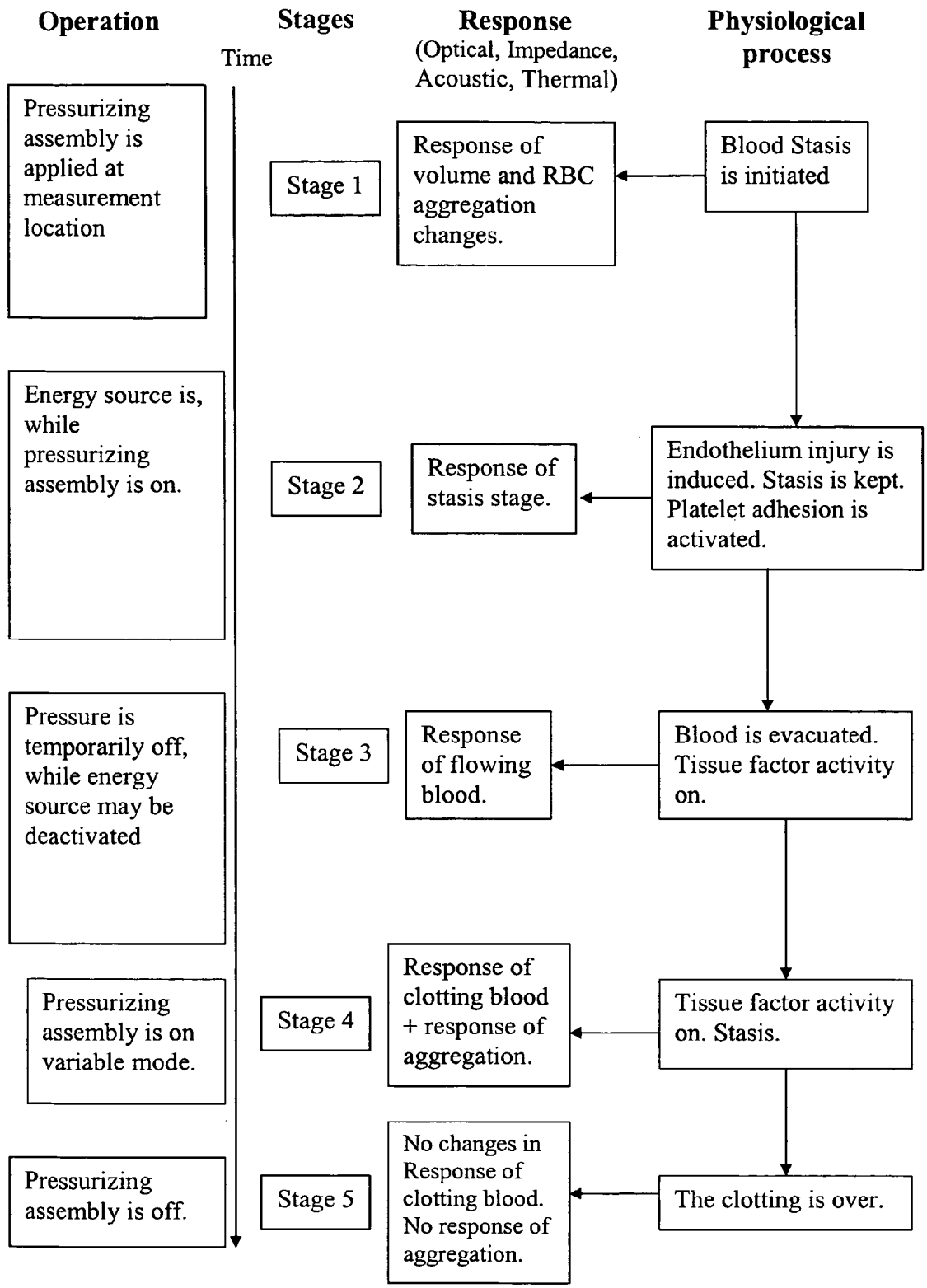
FIG. 3 is a block diagram of specific example of the implementation of the method of FIG. 2.

The following is a specific, but not limiting technical example of the method of the present invention, described with reference to FIG. 3.

In stage 1, pressure (oversystolic) is applied to the location upstream of or in the vicinity of the measurement location (constituting application of a first stimulus), such that blood perturbation or stasis was induced. To this end, a pressurizing cuff may be used operable to provide local squeezing, or an optical fiber or light guide of the light source unit may be used as a pressurizing element. In stage 2, the blood vessels are stimulated by an energy source such as a green laser (constituting application of a second stimulus); generally this may be laser, mechanical, thermal, acoustic or electric current source. Then, in stage 3, the application of pressure is temporarily deactivated and free blood flow is allowed, while the application of energy source may or may not be deactivated. In stage 4, the applied pressure is varied. In this particular example it can be over-systolic, though in general various modifications can be used. Then, in stage 5, the application of pressure is released. In this specific but not limiting example, the optical response of the medium is measured for the medium condition in each of these five stages. Thus, the first stage response is indicative of the volume and RBC aggregation changes, the second stage response is indicative of the stasis condition, the third stage response is indicative of the blood flowing condition, the fourth stage response is indicative of the clotting blood and aggregation condition, and the fifth stage response is indicative of substantially no changes in response of clotting blood and no response of aggregation. Blood stasis is thereby achieved and the time variation of the medium response to thrombus formation condition under the variable application of pressure (e.g. under pressure and after its release) were measured. The measurements included illumination of the medium with several wavelengths and the measured data was in the form of light intensity as a function of time and wavelength.

When thrombosis evolved, the fibrinogen level decreased and intensity and kinetics of the aggregation process changed accordingly. Measurement of the kinetics and intensity of the induced aggregation related signal is a measure of amount of fibrinogen present. The dependence of the parameter(s) mentioned hereinabove upon time, characterize the rate of thrombosis, which can be correlated with prothrombin time test (PT). The absence of the signal change over time (having assymptoted to a maximum level) of at least one measured response is detected and calculated in stage 5.

Actually, the inventive technique can be implemented in several ways utilizing one or more stimuli to cause in vivo at least one micro-coagulation event. Initiating of a micro-coagulation event can be performed by any one or more of the followings means or by their combination: laser impulse; thermal impulse; acoustic impulse; acousto-optical; electrical impulse; and vessels legation.

For example, measurement of a medium response is performed by detecting optical, thermal, acoustic or impedance changes resulting from a local coagulation process. The light response can be measured using for example Optical Coherent Tomography (OCT) technique, or dynamic light scattering technique, or any other coherent optics, particle-size sensitive technique. The light response data can be analyzed using an OCT-based image analysis.

As indicated above, the stimuli may include the application of an unchanging (constant) or a time-varying local pressure so as to reduce the blood flow (up to stasis creation pressure) at the measurement location.

It should also be noted that in some embodiments of the invention, kinetic parameters of Red Blood Cell (RBC) aggregation may be correlated to the relative amount of fibrinogen in the blood. The RBC aggregation may be further used to evaluate a parameter correlative with thrombosis formation time. Also, local oxygen saturation drop at thrombus formation site may be used to evaluate the parameter correlative with the thrombosis formation time. The minimal energy form starting thrombus formation can be measured by analyzing the response curves (kinetic and spectro-kinetic peculiarities of RBC aggregation process indicative of a condition that blood flow secession process has been induced by thrombus formation). A change of local blood volume, derived from optical response may be used as an indication of thrombus formation dynamics. Furthermore, an optically measured change in turbidity of the blood, as a result of fibrin formation, may be derived from the optical response and may be further used as an indication of thrombus formation dynamics. Moreover, a change in the blood particle size, as a result of fibrin formation, may be derived from the optical response and further used as an indication of thrombus formation dynamics.

The following is an example of performing the technique of the present invention on a patient's finger. In this example induction of (i) platelet aggregation and (ii) a change in blood flow is used.

A laser light is used to injure endothelial cells. Thrombi can be generated both in venulas and arterioles. The thrombus generation can be obtained by applying radiation from an argon laser emitting at 514.5 nm with the following parameters: 20 mW, 399 ms, 120 j/sm$^2$. A localized microthrombus/thrombi can be induced providing endothelial damage by platelet adhesion/aggregation. Also, it is known that thermal coagulation can be induced by using laser light of 532 nm, or using a dye laser light of 586 nm) in vitro coagulation, as well as laser illumination employing an argon-ion laser of 517 nm, 100 mW for 1 sec can induce thrombosis. A change in blood flow can be induced by applying pressurizing assembly, such as a blood pressure monitoring pressurized cuff to a measurement location such as an arm or leg. The cuff temporarily stops the blood flow at the measurement location. The resultant microthrombi can be measured by optical or other means.

Figure 4A:
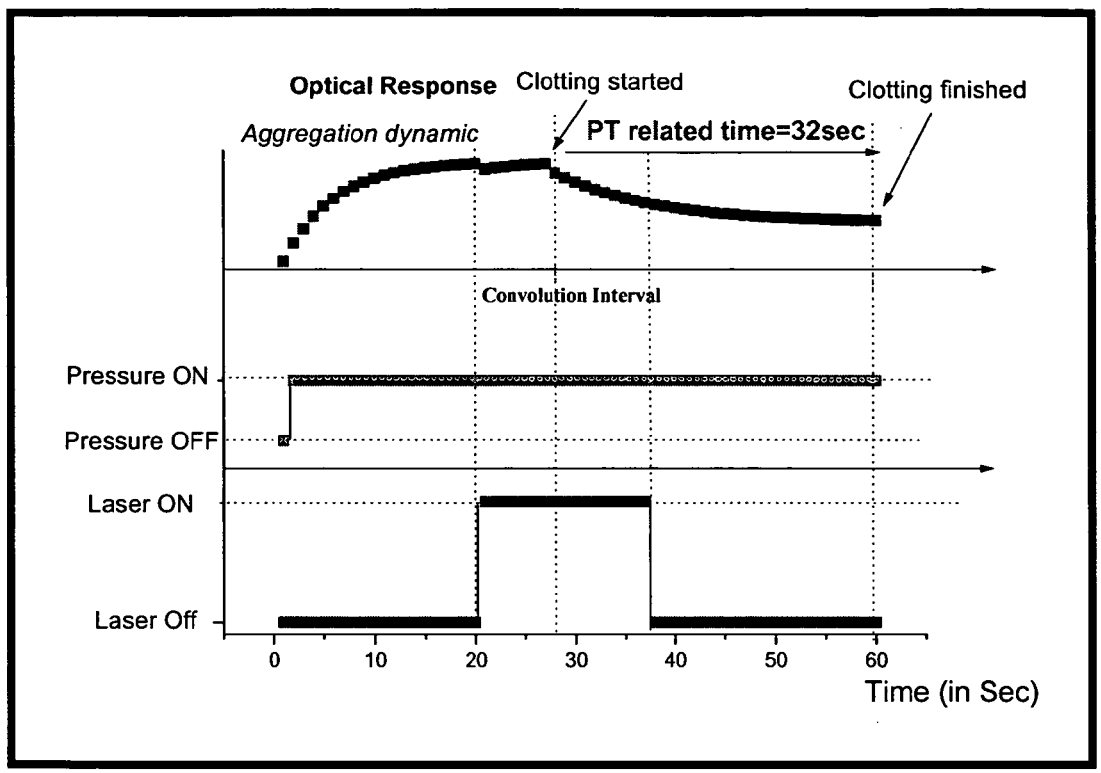
FIGS. 4A and 4B show experimental results of the technique of the present invention.
Figure 4B:
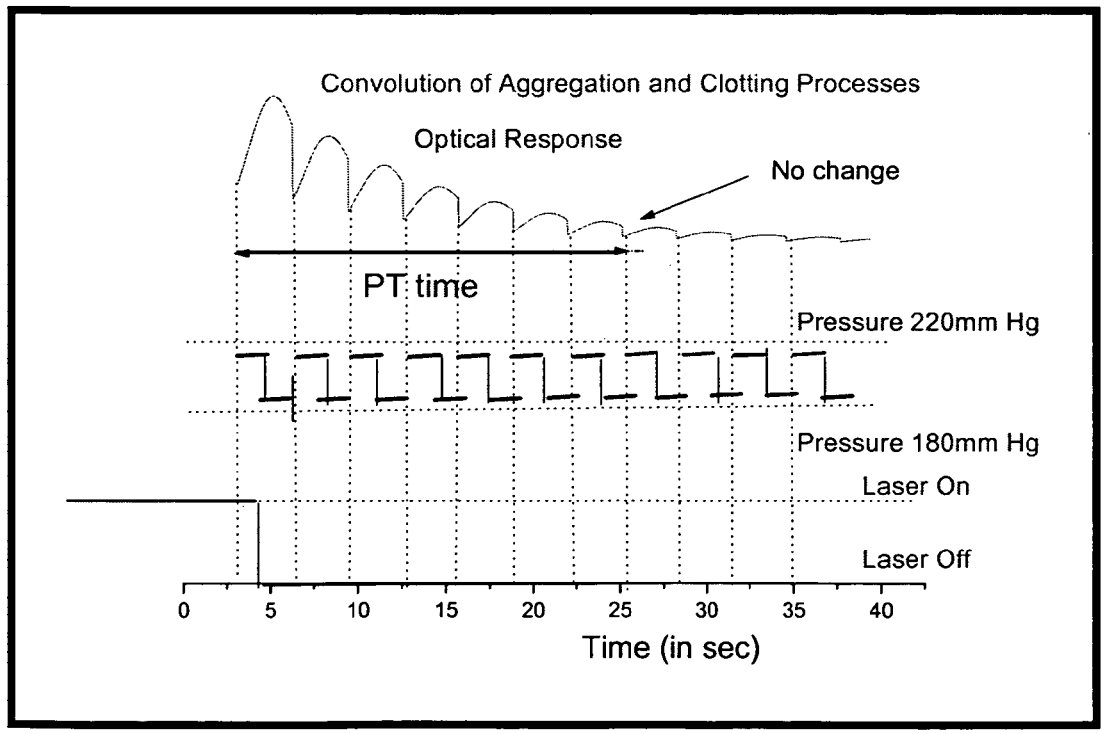

Reference is made to FIGS. 4A and 4B showing the results of two different experiments, respectively. In both examples, measurement of the time dependence of light transmission for a 815 nm wavelength through the region of interest was used, and the application of two stimuli—laser pulsed illumination of a 517 nm wavelength and pressure applied to the vicinity of a measurement location. In the example of FIG. 4A, the laser pulsed illumination and the application of pressure of 200 mm Hg were started substantially simultaneously and concurrently continued for about 60 seconds; and the optical measurements (detection of light reflection) started substantially simultaneously (zero delay time $t_d$) and continued also for about 60 seconds. It is clear from the measured time variation of the optical response that this function is indicative of the successively occurred aggregation dynamics and clotting, the duration of the clotting effect (32 seconds) being indicative of the PT related time.

In the example of FIG. 4B, the laser illumination (first stimulus) was applied first for 25 seconds, and a few seconds (about 3 sec) before the laser illumination was halted the pressure (second stimulus) and the optical measurements were applied (negative delay time $t_d$). The pressure was periodically varying from 180 mmHg to 220 mmHg. The relation (convolution) of the time functions of the stimuli and the time variation of the optical response was determined. This functional is indicative of the PT related time, which is about 18 seconds in the present example.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. In the method claims that follow, alphabetic characters numerals used to designate claim steps are provided for convenience only and do not imply any particular order of performing the steps.

The invention claimed is:

1. A non-invasive method for determination of blood clotting and blood circulation related parameters of a mammal, the method comprising:
    (i) non-invasively inducing at least two stimuli ST in a blood containing medium in the mammal for a preset period of time $t_{ST}$, said at least two stimuli being selected to cause at least one of the following to occur: (a) inducing at least two of three Virchow's triad elements including an abnormality of blood flow, an abnormality of blood constituents, and an abnormality of the blood vessel wall, and (b) inducing a change in red blood cell (RBC) aggregation or local blood viscosity;
    (ii) performing non-invasive measurements at a measurement location in the blood containing medium in the mammal by applying an external field thereto for a preset time period $t_m$, detecting a response of the measurement location to the applied field, and generating measured data indicative thereof; and
    (iii) processing, with a processor, at least a portion of the measured data and processing stimuli related data so as to determine an output data indicative of a relation between a time function of said at least two stimuli ST(t) and a time function of the measured data OR(t), said relation being a predetermined mathematical manipulation between the time function of said at least two stimuli ST(t) and the time function of the measured data OR(t), said output data being indicative of at least one blood circulation and blood clotting related parameter of the mammal.

2. The method according to claim 1, wherein said at least two induced Virchow's triad elements are the abnormality of blood flow, and the abnormality of the blood vessel wall.

3. The method according to claim 1, wherein the abnormality of blood flow comprises at least one of the following: an abnormality of blood rheology, an abnormality of turbulence at bifurcations, and an abnormality of turbulence at a stenotic region.

4. The method according to claim 1, wherein the abnormality of the blood vessel wall comprises at least one of the following: an abnormality of the endothelium, an abnormality of a blood vessel wall thickness, an abnormality of blood vessel wall rigidity, an abnormality of blood vessel wall integrity, an abnormality of blood vessel wall roughness, and an abnormality of plaque concentration.

5. The method according to claim 1, wherein said at least two stimuli are induced in the blood containing medium in the mammal in the vicinity of the measurement location.

6. The method according to claim 1, wherein said inducing of the change in RBC aggregation or local blood viscosity comprises applying an over systolic pressure to the blood containing medium in the mammal to create a stasis state at the measurement location.

7. The method according to claim 1, wherein said inducing of the at least two stimuli includes application of a mechanical pressure of a preset time dependence ST(t)=P(t) to the mammal to at least one of a location different from the measurement location and a location in the vicinity of the measurement location.

8. The method according to claim 1, wherein said non-invasive measurements are optical measurements, the external field being in the form of electromagnetic radiation of at least one predetermined wavelength range, and the response being in the form of electromagnetic radiation of said at least one wavelength range indicative of scattering, reflective, and absorbing properties of the blood containing medium in the mammal at the measurement location.

9. The method according to claim 1, comprising controlling said inducing of the at least two stimuli such that the at least two stimuli vary with time according to a predetermined function for a time period not exceeding said certain time $t_{ST}$.

10. The method according to claim 1, wherein said at least one blood circulation and blood clotting related parameter is indicative of at least one of the following: a condition of thrombosis, a risk of bleeding, and a prothrombin time.

11. The method according to claim 1, wherein said measurement of the time dependence of the response is carried out for at least two different wavelengths of the applied electromagnetic field, the measured data being indicative of the response as the function of time and wavelength; and said relation between the time functions of at least two stimuli and the response being a function of wavelength of the applied field and the time parameter $t_{ST}$ and time delay $t_d$.

12. The method according to claim 11, wherein said at least two different wavelengths of the applied electromagnetic field are in a visible-NIR range.

13. The method according to claim 1, wherein the measured optical response OR, includes at least one of optical transmission T, optical reflection R, and optical scattering of the medium.

14. The method according to claim 1, wherein said at least portion of the measured data to be processed includes the measured data indicative of the response measured from a predetermined moment of time $t_d$ with respect to the end of inducing said at least two stimuli.

15. The method according to claim 14, wherein said predetermined moment of time $t_d$ is selected to satisfy one of the following conditions: it precedes the completeness of the inducing of said at least two stimuli, it substantially coincides with the completeness of the inducing of said at least two stimuli, and it occurs after the completeness of said inducing of the at least two stimuli.

16. The method according to claim 15, wherein while said external field is applied to the measurement location, the response from the measurement location is fixed a certain time $t_d$ after the application of the external field to form said portion of the measured data.

17. The method according to claim 15, wherein said portion of the measured data is indicative of the response detected with a certain time delay $t_d$ from the completeness of the inducing of said at least two stimuli.

18. The method according to claim 15, wherein said time delay $t_d$ is selected to satisfy one of the following conditions: the time delay $t_d$ is negative, said measured data portion corresponding to the measurements starting before said inducing of at least two stimuli is completed; the time delay $t_d$ is substantially zero, said measured data portion corresponding to the measurements starting substantially when said inducing of the at least two stimuli is complete; and the time delay $t_d$ is positive, said measured data portion corresponding to the measurements starting after the inducing of said at least two stimuli is complete.

19. The method according to claim 15, wherein the measured data includes said data portion and data indicative of the detected response before performing said inducing of the at least two stimuli.

20. The method according to claim 1, wherein the output data is indicative of at least one blood parameter selected from: a blood viscosity, a blood rheological property, a blood density, RBC aggregation rate, prothrombin time, a blood clotting parameter, a plasma protein parameter, an erythrocyte sedimentation rate, a fibrin concentration, a fibrinogen concentration, and a drug concentration or concentration of certain product of drug metabolism.

21. An apparatus for use in non-invasive determination of blood clotting related and blood circulation related parameters in a mammal, the apparatus comprising:
 (a) a measurement unit configured and operable for applying an external field to a measurement location in a blood containing medium of the mammal, detecting a response from the measurement location to the applied field, and generating measured data indicative thereof;
 (b) a stimulus inducing device configured and operable to induce at least two stimuli in the blood containing medium in the mammal, said at least two stimuli being of a kind causing at least one of the following to occur: (i) inducing at least two of three Virchow's triad elements in the medium including an abnormality of blood flow; an abnormality of blood constituents, and an abnormality of the blood vessel wall; and (ii) inducing a change in the RBC aggregation;
 (c) a control unit configured for selectively operating said stimulus inducing device to maintain each of said at least two stimuli for a preset period of time $t_{ST}$, for operating the measurement unit to perform measurements and generate the measured, said control unit being preprogrammed to process and analyze the measured data to determine a time function of at least a portion of the measured data and a time function of said at least two stimuli and determine a relation being a predetermined mathematical manipulation between the time variations of said at least two stimuli and the time function of the response, at least portion of the measured data, said mathematical manipulation being indicative of the blood clotting related and blood circulation related parameters in the mammal.

22. The apparatus according to claim 21, wherein the measurement unit is an optical unit comprising a source of electromagnetic radiation of at least one predetermined wavelength range, and an electromagnetic radiation detector for detecting said response and generating said measured data.

23. The apparatus according to claim 21, wherein said stimulus inducing device is configured and operable to induce an abnormality of blood flow, and an abnormality of the blood vessel wall.

24. The apparatus according to claim 23, wherein said stimulus inducing device is configured and operable to induce the abnormality of blood flow by inducing a change in red blood cell (RBC) aggregation.

25. The apparatus according to claim 21, wherein said stimulus inducing device is configured and operable to apply at least one of the following to a location on the mammal: electromagnetic radiation of predetermined wavelength and power, and pressure of a predetermined profile.

26. The apparatus according to claim 21, wherein the control unit operates to create said portion of the measured data corresponding to the measured data indicative of the response measured from a predetermined moment of time $t_d$ with respect to the completeness of the application of said at least two stimuli.

27. An apparatus according to claim 26, wherein said predetermined moment of time $t_d$ is selected to satisfy one of the following condition: it precedes the completeness of the application of said at least two stimuli, it substantially coincides with the completeness of the application of said at least two stimuli, and it occurs after the completeness of the application of the at least two stimuli.

28. The apparatus according to claim 21, wherein the control unit operates to control the operation of the stimulus inducing device to apply the stimulus during certain time $t_{ST}$ such that the stimulus varies with time according to a predetermined function for a time period t not exceeding said certain time $t_{ST}$.

29. The apparatus according to claim 28, wherein the control unit operates to create said portion of the measured data corresponding to the measured data indicative of the response measured from a predetermined moment of time $t_d$ with respect to the completeness of the application of said at least two stimuli and continuing for the time period t larger than $t_d$.

30. The apparatus according to claim 29, wherein said measurement unit is configured for generating the electromagnetic radiation of at least two different wavelengths, the control unit operating to determine the light response as a function of time and wavelength and determine said relation between the time functions of at least two stimuli and the response in the form of a function of wavelength of the applied radiation and the time parameters $t_{ST}$ and $t_d$.

31. The apparatus according claim 22, wherein said stimulus inducing device comprises said source of the electromagnetic radiation.

* * * * *